(12) United States Patent
Rother et al.

(10) Patent No.: US 9,890,406 B2
(45) Date of Patent: Feb. 13, 2018

(54) METHOD FOR PRODUCING CATHINE

(71) Applicant: FORSCHUNGSZENTRUM JUELICH GMBH, Juelich (DE)

(72) Inventors: Doerte Rother, Huerth (DE); Martina Pohl, Aachen (DE); Torsten Sehl, Juelich (DE); Alvaro Gomez Baraibar, BE Delft (NL)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 14/891,823

(22) PCT Filed: May 17, 2014

(86) PCT No.: PCT/DE2014/000256
§ 371 (c)(1),
(2) Date: Nov. 17, 2015

(87) PCT Pub. No.: WO2014/198247
PCT Pub. Date: Dec. 18, 2014

(65) Prior Publication Data
US 2016/0138062 A1    May 19, 2016

(30) Foreign Application Priority Data
Jun. 10, 2013    (DE) .................. 10 2013 009 631

(51) Int. Cl.
*C12N 9/00*    (2006.01)
*C12P 7/26*    (2006.01)
(Continued)

(52) U.S. Cl.
CPC .......... *C12P 13/001* (2013.01); *C12N 9/1096* (2013.01); *C12Y 206/01062* (2013.01);
(Continued)

(58) Field of Classification Search
CPC ........ C12P 13/001; C12P 7/26; C12N 9/1096; C12Y 206/01062; C12Y 401/01001; C12Y 206/01
See application file for complete search history.

(56) References Cited

U.S. PATENT DOCUMENTS

2012/0270899 A1* 10/2012 Bannister ............... A61K 9/08
514/312
2013/0309732 A1* 11/2013 Kao ....................... C12Y 206/01
435/128

FOREIGN PATENT DOCUMENTS

DE    197 36 104    2/1999
WO    WO-02/02753   1/2002

OTHER PUBLICATIONS

Rother et al. ChemCatChem (2011) 13, 1587-1596.*
(Continued)

*Primary Examiner* — Alexander D Kim
(74) *Attorney, Agent, or Firm* — Norris McLaughlin & Marcus, P.A.

(57) ABSTRACT

A method for producing cathine ((1S,2S)-norpseudoephedrine), in which, in a first reaction step, benzaldehyde is reacted with an acetyl donor according to formula (1), where R=H or COOH, by way of an (S)-selective lease to yield an enantiomer mixture according to formulas (2) and (3) and, in a second step, the compound according to formula (3) is reacted with an amine donor by way of an (S)-selective transaminase to yield (1S,2S)-norpseudoephedrine.

11 Claims, 4 Drawing Sheets

(51) Int. Cl.
*C12P 13/00* (2006.01)
*C12N 9/10* (2006.01)

(52) U.S. Cl.
CPC ......... *C12Y 401/01001* (2013.01); *C12P 7/26* (2013.01); *C12Y 206/01* (2013.01)

(56) References Cited

OTHER PUBLICATIONS

Sehl et al. Efficient 2-step biocatalytic strategies for the synthesis of all nor(pseudo)ephedrine isomers., Green Chem., (Apr. 10, 2014), 16, 3341-3348.*
Sehl et al. Two Steps in One Pot: Enzyme Cascade for the Synthesis of Nor(pseudo)ephedrine from Inexpensive Starting Materials., Angewandte Communication. (Epub May 9, 2013) vol. 52, Issue 26, pp. 6772-6775.*
"Stereoselective Synthesis of Norephedrine and Norpseudoephedrine by Usint Asymmetric Transfer Hydrogenation Accompanied by Dynamic Kinetic Resolution" Hyeon-Kyu Lee et al., the Journal of Organic Chemistry 2012, pp. 5454-5460.
"Efficient Synthesis of Ephedra Alkaloid Analogous Using an Enantiomerically Pure N-[(R)-(+)-a-Methybenzyl]aziridine-2-carboxaldehyde" Gwon-Il Hwang et al. from J.Org.Chem. 1996, 61, 6183-6188.
"Asymmetric N1 Unit Transfer to Olefins with a Chiral Nitridomanganese Complex: Novel Stereoselective Pathways to Aziridines or Oxazolines", Masaaki Nishimura et al., J. Org. Chem. 2002, 67, pp. 2101-2110.
Hagel, J.M. et al. Expressed sequence tag analysis of khat (Catha edulis) provides a putative molecular biochemical basis for the biosynthesis of phenylpropyamino alkaloids, In: Genetics and Molecular Biology, vol. 34, 2011, S. 640-646.
Krizevski, R. et al.: Benzaldehyde is a precursor of phenylpropylamino alkaloids as revealed by targeted metabolic profiling and comparative biochemical analyses in Ephedra spp. In: Phytochemistry, vol. 81, 2012, S. 71-79.
Torsten Sehlj et al: Zwei Schritte in einem Reaktionsgefaess: Enzymkasdaden zur selektiven Synthese von Nor (pseudo) ephedrio aus kostenguenstigen Ausgangsmaterialien:, Angewandte Chemie (International Ed. In English), vol. 125, No. 26, May 9, 2013 (May 9, 2013), pp. 6904-6908, XP055134536, ISSN: 0044-8249, DOI: 10.1002/ange.201300718 the whole document.
D. Rother et al: "S-Selective Mixed Carboligation by Structure-Based Design of the Pyruvate Decarboxylase from Acetobacter pasteurianus," Chemcatchem, vol. 3, No. 10, Aug. 31, 2011 (Aug. 31, 2011), pp. 1587-1596, XP055134569, ISSN: 1867-3880, DOI: 10.1002/cctc.201100054 the whole document.
Tina Gerhards et al: "Influence of Organic Solvents on Enzymatic Asymmetric Carboligations", Advanced Synthesis & Catalysis, vol. 354, No. 14-15, Oct. 4, 2012 (Oct. 4, 2012), pp. 2805-2820, X1055134571, ISSN: 1615-4150, DOI: 10.1002/adsc.201200284 the whole document.
Torsten Sehl et al: Efficient 2-step biocatalytic strategies for the synthesis of all nor0Pseudo) ephedrine isomers:, Green Chemistry, vol. 16, No. 6, Jan. 1, 2014 (Jan. 1, 2014), pp. 3341, XP055124877, ISSN: 1463-9262, DOI: 10.1039/c4gc00100a the whole donoment.

* cited by examiner

METHOD FOR PRODUCING CATHINE

BACKGROUND OF THE INVENTION

The invention relates to a method for producing cathine.

Cathine ((1S,2S)-norpseudoephedrine) can be extracted from the leaves of khat and is frequently used as an appetite suppressant. Due to the sympathomimetic function stimulating the autonomic nervous system, it is used as a cardiovascular drug.

A variety of methods are already known from the prior art for synthetic production.

A 7-step synthesis is known, for example, from the publication "Stereoselective Synthesis of Norephedrine and Norpseudoephedrine by Using Asymmetric Transfer Hydrogenation Accompanied by Dynamic Kinetic Resolution" by Hyeon-Kyu Lee at al. in the Journal of Organic Chemistry 2012, pgs. 5454-5460.

The publication "Efficient Synthesis of Ephedra Alkaloid Analogous Using an Enantiomerically Pure N-[(R)-(+)-α-Methylbenzyl]aziridine-2-carboxaldehyde" by Gwon-Il Hwang at al. from J. Org. Chem, 1996, 61, 6183-6188, discloses a method for producing cathine with high enantiomeric excess, which is based on an enantiomerically pure substrate and is very expensive.

Other methods, as described, for example, in the publication "Asymmetric N1 Unit Transfer to Olefins with a Chiral Nitridomanganese Complex: Novel Stereoselective Pathways to Aziridines or Oxazolines" by Masaaki Nishimura at al., disclose methods in which cathine is formed as a by-product.

It is therefore the object of the invention to make a simple method for producing cathine available, which overcomes the disadvantages of the state of the art, requires only few reaction steps, is inexpensive, results in high enantiomeric and diastereomeric purity and in a high yield, and requires as few processing steps as possible. The method should be easily scalable.

Using the method according to the invention, cathine can be produced in enantiomeric purity of >99% and diastereomeric purity of 70%, and in one advantageous embodiment of up to 97%. Conversion of 90% can be achieved. For this purpose, commercially available starting materials may be used. The method necessitates few processing steps, is easy to scale, and can be carried out as a one-pot reaction.

The invention will be described hereinafter in the general form thereof.

(S)-selective enzyme within the meaning of the invention is an enzyme that results in an (S)- configured product.

In a first reaction step, benzaldehyde is reacted in vitro with an acetyl donor according to formula (1)

Formula (1)

by way of an (S)-selective lyase to yield an enantiomer mixture of the compounds according to formulas (2) and (3)

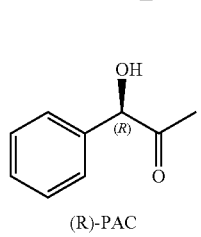

Formula (2)

(R)-PAC

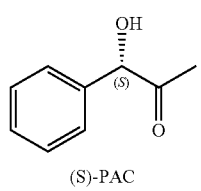

Formula (3)

(S)-PAC wherein the abbreviation PAC denotes phenylacetylcarbinol.

The acetyl donor according to formula (1) can be acetaldehyde where R=H or pyruvate where R=COOH.

Figure 1:
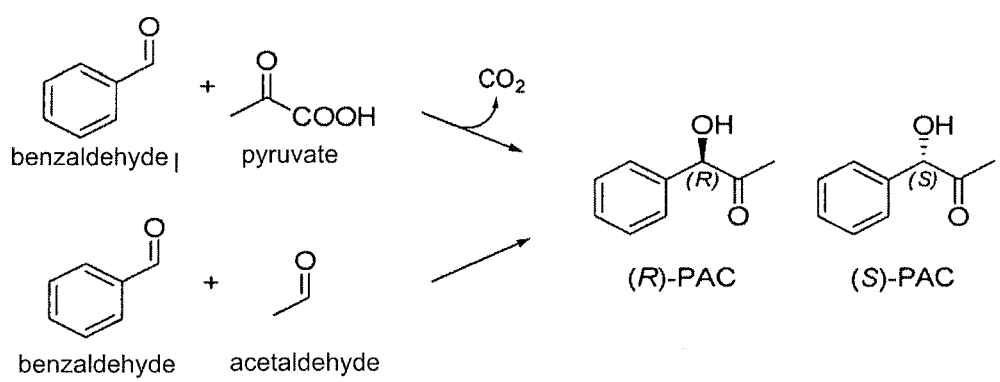
FIG. 1 is an example of the reaction pathway.

The reaction pathway is shown by way of example in FIG. 1.

The lyase may be, for example, an (S)-selective lyase from *Acetobacter*, in particular *Acetobacter pasteurianus*, in particular the ApPDC-E4690 variant.

Preferably, purified and lyophilized enzymes are used. Lyophilization has the advantage that the enzymes are stable and high enzyme concentrations can be used; in addition, purified enzymes result in considerably higher optical purities, which is to say high enantiomeric and diastereomeric excess of the product.

Furthermore, cofactors can be used for the (S)-selective lyase, which increase the conversion.

For example, magnesium ions such as magnesium sulfate or magnesium chloride, together with thiamine diphosphate can be used as cofactors.

When magnesium sulfate and thiamine diphosphate are used as cofactors, a concentration range of 1 to 5 mM, and preferably 2.5 mM, for magnesium sulfate and of 5 to 300 μM, and preferably 100 μm, for thiamine diphosphate is preferred.

The reaction can be carried out at a pH value of 5 to 8, and preferably of 6 to 7.5.

For this purpose, a potassium phosphate buffer can be used, for example. However, buffers such as HEPES, MOPS, TEA or TRIS-HCl are also possible.

The preferred temperature range is room temperature, but the reaction can also be carried out well between 20° C. and 30° C., and more particularly 25° C.

The reaction is preferably carried out at atmospheric pressure.

As an alternative, the enzymatic reaction can take place in vivo. This has the advantage that the enzyme can be produced cost-effectively as a catalyst.

For this purpose, *E. coli*. bacteria can be used as production organisms.

Genes coding for a lyase in the first step can be ligated into a vector.

The *E. coli* strains are preferably recombinant and contain plasmids that carry genes for an (S)-selective lyase.

The plasmids can preferably include genes for the above-mentioned lyases.

For example, pET22b or pKK233 base structures, which include the corresponding lyase genes, can be used as plasmids.

The production organisms secrete the desired product according to formulas (2) and (3) into the aqueous solution.

In a preferred embodiment of the method according to the invention, the undesirable compound according to formula (2)

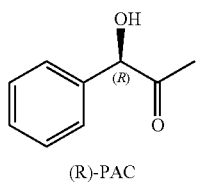

Formula (2)

(R)-PAC is reacted by way of a benzaldehyde lyase to yield benzaldehyde and acetaldehyde.

Figure 2:
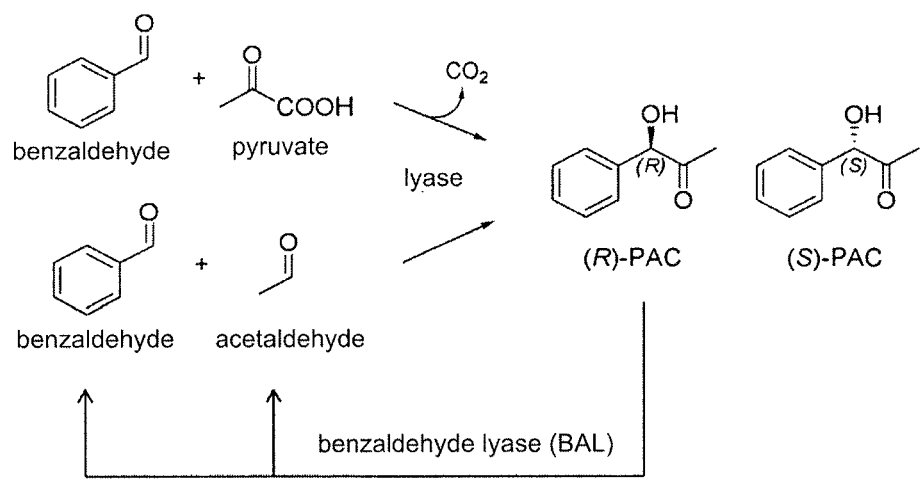
FIG. 2 shows the reaxtion scheme.

The reaction scheme is shown in FIG. 2.

This has the advantage that the undesirable by-product according to formula (2) is cleaved, and the resultant benzaldehyde and acetaldehyde are returned to the process, increasing the yield of the desired product according to formula (3). The enantiomeric excess of (S)-PAC according to formula (3) can be increased in total to >97%. The yield in this step is 95%, based on the total amount of PAC used.

In the reaction of the compound according to formula (2), it is advantageous to add an excess of the acetyl donor during the reaction process, so that sufficient acetyl donor is available for the further reaction to yield the desired intermediate compound according to formula (3). This is advantageous in particular with volatile acetyl donors, such as acetaldehyde. For example, a 10-fold excess of acetyl donor compared to the benzaldehyde can be used.

The intermediate product is preferably separated off. For this purpose, column chromatography with silica gel can be used, using petroleum ether:ethyl acetate (90:10) as the separating liquid.

The compound according to formula (3) thus obtained is reactd in a second reaction step with an amine donor by way of an (S)-selective transaminase to yield the cathine end product ((1S,2S)-norpseudoephedrine). The reaction is shown schematically in FIG. 3.

Transaminases which convert the substrate and are (S)-selective can be used for the second reaction step, which is the chemical reductive amination. The transaminase can be from *Chromobacterium*, such as *Chromobacterium violaceum*, preferably CV2025. Furthermore, transaminases from *Alcaligens denitrificans*, *Arthrobacter citreus*, *Bacillus megaterium*, *Pseudomonas fluorescens*, *Vibrio fluvialis* or *Caulobacter crescentus* may be used.

Preferably, purified and lyophilized enzymes are used. Lyophilization has the advantage that the enzymes are stable and high enzyme concentrations can be used; in addition, purified enzymes result in considerably higher optical purifies, which is to say high enantiomeric and diastereomeric excess of the product.

(S)-alpha-methylbenzylamine, benzylamine, isopropylamine, L-alanine, (±)-1-methyl-3-phenylpropylamine, (±)-1-aminoindane can be used as amine donors, for example.

Pyridoxal 5'-phosphate can be used as a cofactor.

The pyridoxal 5'-phosphate concentration preferably ranges between 100 and 200 μM.

The reaction can be carried out in an aqueous medium in a pH range of 6 to 11, and preferably of 7.5 to 8.5.

Suitable buffers, such as HEPES, potassium phosphate, MOPS, TEA or TRIS-HCl, can be used for this purpose.

The preferred temperature range is 25° C., but the reaction can also be carried out well in a range of 20° C. to 30° C.

The reaction is preferably carried out at atmospheric temperature.

As an alternative, the enzymatic conversion with the (S)-selective transaminase can take place in vivo.

For this purpose, *E. coli* bacteria can be used as production organisms.

Genes coding for a transaminase can be ligated into a vector.

The *E. coli* strains are preferably recombinant and contain plasmids that carry genes for a (S)-selective transaminase.

The plasmids can preferably include genes for the above-mentioned transaminases.

For example, pET29a or pKK233 base bodies, which include the corresponding transaminase genes, can be used as plasmids.

The production organisms secrete the desired product according to formula (3) into the aqueous solution.

The reactions in vivo can be carried out in the method according to the invention either only for the first or the second reaction step, or for both reaction steps 1 and 2. The remaining conditions can be selected for each step in the same manner as for the enzymatic reaction in vitro.

Figure 3:
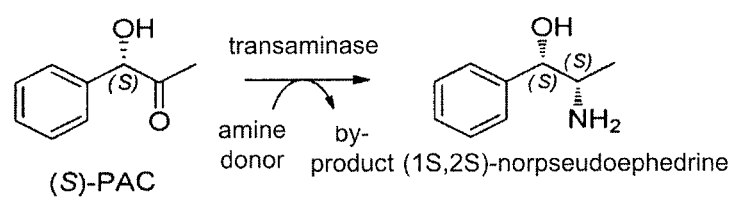
FIG. 3 shows the transaminase.
Figure 4:
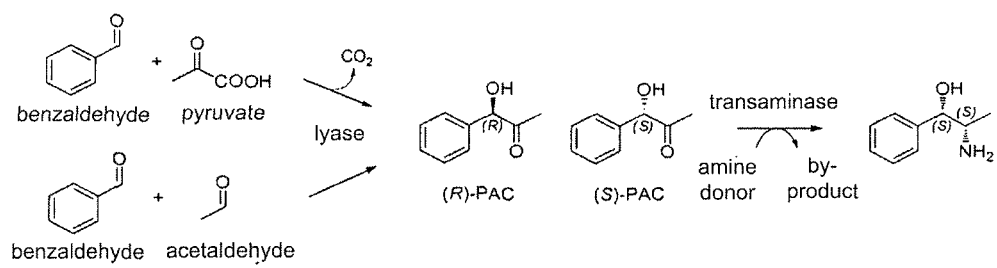
FIG. 4 shows a summary of the steps from FIGS. 1 and 3.

FIG. 4 shows a summary of the steps from FIGS. 1 and 3.

EXAMPLE

The 2-step synthesis was successfully carried out with the combination of the (S)-selective lyase ApPDC-E469G from the organism *Acetobacter pasteurianus* in the first step and the (S)-selective transaminase CV2025 from the organism *Chromobacterium violaceum* in the second step. In the first step, acetaldehyde is combined directly with benzaldehyde or pyruvate following decarboxylation to yield acetaldehyde with benzaldehyde, to yield the (S)-PAC having an enantiomeric purity of approximately 70%. The yield after processing was 95%, the ee was approximately 70%. The conversion in the second reaction step was 95%. In total, a total conversion into cathine of approximately 90%, with optical purity of ee>99% and de of approximately 70%, was achieved across the two reaction steps.

Reaction Conditions:

Step 1 (lyase reaction, FIG. 1):

40 mM benzaldehyde, 400 mM pyruvate, 2.5 mM magnesium sulfate, 100 μm thiamine diphosphate, 0.5 mg/mL ApPDC-E469G (purified lyophilized enzyme), 100 mM potassium phosphate buffer, 25° C., reaction time 48 h. Subsequently, extraction and column chromatography purification of the product ((S)-PAC) were carried out. The yield was 95%. Alternatively, the reaction can also be carried out with acetaldehyde instead of pyruvate and/or with whole cells, in which the ApPDC-E469G enzyme is present in overexpressed form, rather than with the purified enzyme.

Step 2 (transaminase reaction, FIG. 3)

10 mM (S)-PAC, 10 mM (S)-alpha-methylbenzylamine, 1 mg/ml purified enzyme, 25° C., 100 mM HEPES with 0.1 mM pyridoxal 5'-phosphate, pH 7.5, reaction time 24 h. The conversion was 95%. The reaction can alternatively also be catalyzed with whole lyophilized cells, in which the (S)-selective transaminase is present in overexpressed form.

An additional step, following the lyase reaction, can optionally be used to increase the enantiomeric purity of the intermediate ((S)-PAC). Pyruvate, ApPDC-E469G and benzaldehyde lyase from the *Pseudomonas fluorescens* organism are added to the purified (S)-PAC (ee approximately 70%). The benzaldehyde lyase catalyzes the selective cleavage reaction of (R)- PAC to yield benzaldehyde and acetaldehyde. Analogously to reaction step 1, the resultant benzaldehyde is used as the substrate for the carboligation reaction of benzaldehyde and pyruvate to yield (S)-PAC which is catalyzed successively by the ApPDC-E469G enzyme. The ee of the product can thus be increased to ee >97% (S)-PAC if both the benzaldehyde lyase and ApPDC-E469G are present in the reaction batch. The yield is >91%, based on the total amount of PAC used in this step. Increase in enantiomeric purity of (S)-PAC in FIG. 2:

a) 11.2 mM (S)-PAC (ee approximately 70%), 200 mM pyruvate, 2.1 mg/mL ApPDC-E469G, 2 mg/mL BAL (benzaldehyde lyase), 2.5 mM magnesium sulfate, 100 µM thiamine diphosphate, 100 µM potassium phosphate buffer, 25° C., reaction time: 48 h. Yield: 91.6%, ee((S)-PAC)= 97.4%.

b) 20.7 mM (S)-PAC (ee approximately 70%), 300 mM pyruvate, 2.1 mg/mL ApPDC-E469G, 2 H mg/mL BAL (benzaldehyde lyase), 2.5 mM magnesium sulfate, 100 µM thiamine diphosphate, 100 µM potassium phosphate buffer, 25° C., reaction time 48 h. Yield 93.7%, ee((S)-PAC)= 96.7%.

The invention claimed is:

1. A method for producing (1S,2S)-norpseudoephedrine, comprising:

a first step of reacting benzaldehyde with an acetyl donor according to formula (1)

formula (1)

where R=H or COOH in the presence of an (S)-selective lyase to yield an enantiomer mixture comprising compounds according to formulas (2) and (3)

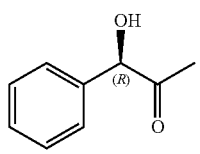

Formula (2)

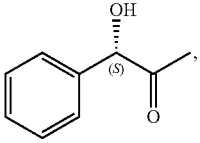

Formula (3)

and a second step of reacting the compound according to formula (3) with an amino donor in the presence of an (S)-selective transaminase to yield (1S,2S)-norpseudoephedrine, wherein in the first step, a magnesium salt and thiamine diphosphate are used as cofactors, and E469G variant of *Acetobacter pasteurianus* pyruvate decarboxylase (ApPDC-E469G) is used as the (S)-selective lyase, and in the second step, pyridoxal 5'-phosphate is used as a cofactor, and CV2025 from *Chromobacterium violaceum* is used as the (S)-selective transaminase.

2. The method according to claim 1, wherein the first step is carried out at a pH value of 5 to 9.

3. The method according to claim 1, comprising contacting the compound according to formula (2) with a benzaldehyde lyase to yield benzaldehyde and acetaldehyde.

4. The method according to claim 1, comprising adding an excess of the acetyl donor in the first step.

5. The method according to claim 1, comprising a step of separating the compound according to formula (3) from the enantiomer mixture prior to beginning the second step.

6. The method according to claim 1, wherein the amine donor used in the second step is a component comprising methylbenzylamine, benzylamine, isopropylamine, L-alanine, (±)-1-methyl-3-phenylpropylamine or (±)-1-aminoindane.

7. The method according to claim 1, wherein the second step is carried out at a pH value of 6 to 11.

8. The method according to claim 1, comprising using purified and lyophilized enzymes in one or both of the first step and the second step.

9. The method according to claim 1, wherein one or both of the first step and the second step are carried out in vivo.

10. The method according to claim 9, comprising using *E. coli* as a production strain.

11. The method according to claim 9, comprising ligating genes coding for the (S)-selective lyase in the first step, or the (S)-selective transaminase in the second step, or both the (S)-selective lyase and the (S)-selective transaminase, into a vector.

* * * * *